United States Patent
Seiler et al.

(10) Patent No.: US 9,877,868 B2
(45) Date of Patent: Jan. 30, 2018

(54) APPARATUS FOR DISSECTING AN EYE FOR THE INTRODUCTION OF A PHOTOSENSITIZER

(71) Applicant: Novartis AG, Basel (CH)

(72) Inventors: Theo Seiler, Zürich (CH); Katrin Skerl, Erlangen (DE); Yao Zhang, Erlangen (DE)

(73) Assignee: Novartis AG, Basel (CH)

( * ) Notice: Subject to any disclaimer, the term of this patent is extended or adjusted under 35 U.S.C. 154(b) by 171 days.

(21) Appl. No.: 14/417,092

(22) PCT Filed: Oct. 9, 2013

(86) PCT No.: PCT/EP2013/071011
§ 371 (c)(1),
(2) Date: Jan. 23, 2015

(87) PCT Pub. No.: WO2015/051832
PCT Pub. Date: Apr. 16, 2015

(65) Prior Publication Data
US 2015/0342784 A1    Dec. 3, 2015

(51) Int. Cl.
*A61F 9/008* (2006.01)
*A61B 17/34* (2006.01)

(52) U.S. Cl.
CPC ...... *A61F 9/00825* (2013.01); *A61B 17/3421* (2013.01); *A61F 2009/00872* (2013.01)

(58) Field of Classification Search
CPC .................. A61N 5/062; A61F 9/008–9/009
See application file for complete search history.

(56) References Cited

U.S. PATENT DOCUMENTS

| 5,254,106 | A | 10/1993 | Feaster |
| 8,409,177 | B1 * | 4/2013 | Lai .......................... A61F 9/008 606/4 |
| 2008/0051772 | A1 | 2/2008 | Suckewer et al. |
| 2011/0282160 | A1 | 11/2011 | Bhadri et al. |
| 2012/0150158 | A1 * | 6/2012 | Krause ............... A61F 9/00825 606/4 |
| 2013/0310728 | A1 * | 11/2013 | Seiler ..................... A61N 5/062 604/20 |

FOREIGN PATENT DOCUMENTS

| EP | 1175879 A1 | 1/2002 | |
| EP | 2407132 A1 * | 1/2012 | ......... A61F 9/00827 |
| WO | 03005920 A1 | 1/2003 | |
| WO | 2007044967 A2 | 4/2007 | |
| WO | 2011037941 A1 | 3/2011 | |

* cited by examiner

*Primary Examiner* — Nathan J Jenness (57) ABSTRACT

An apparatus for dissecting an eye for the introduction of a photosensitizer into tissue of an eye, a cannula device for introducing the photosensitizer, a system comprising the apparatus and the cannula device, and a method for dissecting an eye for the introduction of a photosensitizer are provided. The apparatus comprises a source for laser radiation, a system for guiding and focusing the laser radiation with respect to the tissue of an eye, and a computer for controlling said system.

14 Claims, 4 Drawing Sheets

APPARATUS FOR DISSECTING AN EYE FOR THE INTRODUCTION OF A PHOTOSENSITIZER

CROSS REFERENCE TO RELATED APPLICATIONS

This application is a section 371 national stage phase of International Application No. PCT/EP2013/071011, filed 9 Oct. 2013, titled "APPARATUS FOR DISSECTING AN EYE FOR THE INTRODUCTION OF A PHOTOSENSITIZER," which is hereby incorporated by reference in its entirety.

TECHNICAL FIELD

The present invention generally relates to refractive surgery, i.e. corneal surgery, for example, LASIK, and related ophthalmological procedures. More particularly, embodiments of the present invention relate to an apparatus for dissecting an eye for the introduction of a photosensitizer into tissue of an eye, a cannula device for introducing the photosensitizer, a system comprising the apparatus and the cannula device, and a method for dissecting an eye for the introduction of a photosensitizer.

BACKGROUND

In ophthalmology, the technique of using a photosensitizer and electromagnetic radiation to change the biomechanical and biochemical properties of tissue, in particular the cornea, for therapeutic purposes has been known for more than 10 years.

The human eyeball is bounded by the corneosclera. Due to internal eye pressure, the corneosclera, which contains collagen, has an approximately spherical shape. In the posterior eyeball region, the corneosclera consists of white sclera. The cornea, which is transparent to visible light, is situated in the anterior region.

Deformations of the corneosclera can cause ametropia. For example, axial myopia, a type of myopia, can result from a sclera longitudinal expansion of the eyeball. An ellipsoidal shaped corneal surface can cause a form of astigmatism or other high order aberration, which is also called "irregular corneal curvature". Another defect of the cornea is keratoconus, in which a pathological softening of the cornea leads to a progressive thinning and cone-shaped deformation of the cornea. As the bulging increases, the cornea becomes thinner below the center. It can fracture and become scarred, which can permanently reduce visual acuity.

In known techniques, the corneal epithelium is at least partially removed to introduce riboflavin into the cornea, because the epithelium hinders the riboflavin from penetrating the cornea by acting as a barrier to the diffusion of the riboflavin molecules into the cornea. The removal of the epithelium is, however, usually painful for the patient and the subsequent healing process may have complications.

SUMMARY

Certain embodiments relate to a system for dissecting an eye for the introduction of a photosensitizer into tissue of an eye, the system comprising the apparatus and the cannula device. Certain embodiments relate to an apparatus for dissecting an eye for the introduction of a photosensitizer into tissue of an eye, and the apparatus comprises a source for laser radiation, a system for guiding and focusing the laser radiation relative to the tissue of an eye and a computer for controlling the aforementioned system. Certain embodiments relate to a cannula device for introducing a photosensitizer into tissue of an eye. Certain embodiments relate to an appropriate method for dissecting an eye using laser radiation for the introduction of photosensitizer into tissue of an eye.

The photosensitizer can be introduced into an eye to change the biomechanical and/or biochemical properties of the eye in a process known as "corneal crosslinking" or, in short, "crosslinking".

There are complex dependencies which militate against routine use of crosslinking therapy on the eye. The relationships between the doses of the electromagnetic radiation and photosensitizer and their effect on and in the tissue of an eye are wide ranging. The dose of electromagnetic radiation relates to the intensity of the electromagnetic radiation and its distribution in space and time. The dose of the photosensitizer relates to the chemical structure, concentration and reactions in space and time of the photosensitizer. The effects of different radiation and photosensitizer doses on and in the eye of a patient are strongly dependent on the patient's characteristics. In certain situations, the effect of the crosslinking produced by the radiation and the photosensitizer can be undesirable, and may even result in damaging the tissue or impairing the functioning of the eye. It is therefore desirable to provide precise dosages of photosensitizer with a defined concentration gradient across the cornea.

The photosensitizer may comprise any suitable ingredients that stabilize corneal tissue, e.g., riboflavin (vitamin B2), lysyloxidase, transglutaminase, sugar aldehydes, ethylcarbodiimid, glutaraldehyde, formaldehyde or mixtures of these e.g., Karnovsky solution.

It is the object of certain embodiments to provide an apparatus and a method for dissecting an eye for the introduction of a photosensitizer in the tissue, a cannula device for introducing the photosensitizer and a system comprising the apparatus and the cannula device. The embodiments may be used to uniformly distribute the photosensitizer in the eye. In all the developments and embodiments a gas, especially air, may also be injected into one or more channels.

According to a first aspect, an apparatus for dissecting an eye for the introduction of a photosensitizer into tissue of the eye is provided. The apparatus comprises a source of laser radiation, a system for guiding and focusing the laser radiation with respect to the tissue of the eye, and a computer for controlling said system. The computer is programmed to control the laser radiation to create in the tissue of the eye at least one insertion channel that extends at least partially into the stroma of the eye. The at least one insertion channel is connected to at least one opening in the surface of the eye and extends substantially in radial direction with respect to a point on an axis of the eye. These openings through which the channels are accessible from outside may be arranged at or near the border of the cornea, i.e., at or near the limbus. The openings may be cut into the surface of the eye, e.g., by cutting opening incisions into the surface by means of a laser inducted optical breakthrough. However, the channels may be reached with a cannula device, which will be described in more detail below, directly without cutting openings into the surface.

The computer is further programmed to control the laser radiation to create in the tissue of the eye two or more side channels. The two or more side channels are associated with the at least one insertion channel. The two or more side channels respectively extend away from the associated at least one insertion channel in a direction different from the radial direction.

The axis of the eye may be any suitable axis in or defined with reference to the eye. For example, the axis of the eye may be the optical axis of the eye, the visual axis of the eye or the virtual axis of the eye, also known as line of sight. The radial direction may be understood as any radial direction with respect to any point along or on the axis of the eye, e.g., the optical axis of the eye. For example, the radial direction may be understood as any radial direction with respect to the center of the surface of the eye. The radial direction may also be understood as any radial direction with respect to the axis of the eye. For example, "radial" may be construed to mean directed outwards starting from the apex of the cornea. Alternatively, "radial" may be construed to mean directed outwards starting from the vertex of the cornea, the virtual axis of the cornea or the optical or visual axis of the cornea.

The tissue of the eye may comprise the cornea or the capsular bag. For example, photosensitizer may be introduced into the capsular bag from the lens. As a result it is possible to introduce the photosensitizer without having to remove or open up parts of the cornea. For example, a cannula, which may be in the form of the cannula device as explained below, may be inserted through the opening into the at least one insertion channel. The cannula device may then output the photosensitizer into the two our more side channels so as to introduce the photosensitizer into the side channels. The photosensitizer can then diffuse through the two or more side channels, the at least one insertion channel and the remaining tissue of the eye. In this way, the photosensitizer may then be uniformly distributed in the eye.

The laser radiation can be used to create channels, e.g., the at least one insertion channel and the two or more side channels. Examples of sources of laser radiation include an attosecond laser, a femtosecond laser, a nanosecond laser, or a picosecond laser. In certain cases, a LASIK procedure or lenticule incisions may be used. In such procedures, a femtosecond laser cuts tissue of the eye by photodisruption of the tissue with the energy of the laser light, which creates laser inducted optical breakthroughs (LIOB), which generates also the cavitation bubbles. In LASIK procedure, the laser system cuts a flap or cap in the stroma. The flap/cap is lifted or removed to ablate the exposed stroma using, e.g., an excimer laser in order to reshape the cornea. Pulsed lasers with pulse lengths in the picosecond, nanosecond and attosecond range are also suitable for creating the at least one insertion channel and the two or more side channels.

The term "channel" as used in certain embodiments does not mean an incision area for creating a flap/cap as in LASIK. In addition, the term "channel" may refer to one, two, or more channels.

In certain embodiments, the system for guiding and focusing the laser radiation relative to the eye can be used to create channels. According to certain embodiments, the computer controlling the optical system for guiding and focusing the laser radiation may be programmed to move the foci of the laser radiation along a straight or curved line to yield LIOBs in the tissue in order to produce the at least one insertion channel and the two or more side channels. The at least one insertion channel and the two or more side channels may be created such that, on the one hand, the separation of the individual adjacent LIOB from each other (or "spacing" between the bubbles) may impair the structure and stability of the tissue as little as possible. On the other hand, the separation between the LIOBs forming the channels may be so small that the photosensitizer, introduced into the two or more side channels in the form of a solution penetrates into the tissue through the two or more side channels and the at least one insertion channel in the desired manner, i.e., from LIOB to LIOB. In the regions between adjacent LIOBs, the photosensitizer therefore penetrates by diffusion. It follows that in the sense of certain embodiments the term "channel" is not necessarily to be thought of as a continuous cavity fully free of tissue, although on the other hand completely continuous channels can also be envisaged in certain embodiments.

The at least one insertion channel and the two or more side channels may at least partially be created by the laser radiation, wherein the LIOBs at least in part do not merge completely with one another. The distance between adjacent LIOBs may be in the range from 1 μm to 20 μm. For example, distance between adjacent LIOBs may be in the range from e.g., 1 μm to 10 μm; 3 μm to 5 μm; 7 to 10 μm; 10 to 15 μm.

In accordance with a first variant of the apparatus according to the first aspect, the two or more side channels may respectively extend substantially in a circumferential direction around any point on the axis of the eye, e.g., the optical axis, the virtual axis or any other suitable axis of the eye. The cannula device may then output the photosensitizer into the two our more side channels so as to introduce the photosensitizer into the side channels. The photosensitizer can then diffuse through the two or more side channels, the at least one insertion channel and the remaining tissue of the eye. In this way, the photosensitizer may then be uniformly distributed in the tissue of the eye.

For example, the at least one insertion channel may extends substantially in radial direction with respect to a point on the optical axis of the eye and with respect to a point on the optical axis of the eye and the two or more side channels may respectively extend substantially in a circumferential direction around the same point on the optical axis of the eye. Said point may be the center of the surface of the eye. In other words, the two or more side channels may respectively extend substantially in a circumferential direction around the axis of the eye. For example, the two or more side channels may be at least approximately shaped according to a perimeter of a sector of a circle or any other geometrical form.

A first subset of the two or more side channels may extend away from the at least one insertion channel in the direction different from the radial direction at a first position along the radial direction. A second subset of the two or more side channels may extend away from the at least one insertion channel in the direction different from the radial direction at a second position along the radial direction different from the first position. Additional subsets may further extend away from the at least one insertion channel at positions in the radial direction which are different from the first and second positions. The first, second and further positions may be regarded as branching points of the two or more side channels from the at least on insertion channel. The first and/or second subset may comprise any number of side channels, e.g., one, two, three, four or more than four side channels. For example, the first and second subset may be a pair of side channels.

In accordance with a second variant of the apparatus according to the first aspect, which may be realized independent from or in combination with the first variant of the apparatus according to the first aspect, each of the two or more side channels may be arranged in an angular shape. The two or more side channels may be formed such that at least a subset of the side channels reconnects with each other. For example, in case of a pair of side channels, angularly shaped side channels may reconnect to form a pair of side channels in the form of a rhombus.

The cross-section of the at least one insertion channel may be different from or the same as the cross-section of the two or more side channels. For example, the cross-section of the at least one insertion channel may be larger than the cross-section of the two or more side channels. The width of a channel, e.g., the width of the at least one insertion channel and/or the width of the two or more side channels, may lie in the range from 0.1 mm to 1.2 mm, although every subinterval therein is also disclosed here.

In accordance with a conceivable embodiment of the apparatus according to the first aspect, the computer may be programmed to control the laser radiation to create in the tissue of the eye a plurality of insertion channels. Each of the plurality of insertion channels may extend substantially in radial direction with respect to the point on the axis of the eye. The computer may further be programmed to control the laser radiation to create in the tissue of the eye two or more side channels associated with each of the plurality of insertion channels. The two or more side channels may respectively extend away from the associated insertion channel of the plurality of insertion channels in a direction different from the radial direction.

Although all of the plurality of insertion channels may extend in radial direction, the direction of each of the insertion channels may be different from each other. For example, the insertion channels may respectively extend between the point on the optical axis and the periphery of the cornea in a pattern like the spokes of a wheel.

In circumferential direction, the insertion channels may be equally distributed. For example, the same angle may lie between each neighboring insertion channel. The angle between the neighboring insertion channels may be e.g., 180 degrees, 90 degrees, 45 degrees or any other conceivable angle.

The computer may be programmed to control the laser radiation to create in the eye each of the plurality of insertion channels at a respective segment of a plurality of segments of the eye.

In accordance with a first variant of the conceivable embodiment of the apparatus according to the first aspect, two side channels (a pair of side channels) may be respectively associated with each of the multiple insertion channels. Each of the pairs of side channels may extend away from the associated insertion channel in circumferential direction with respect to the point on the optical axis of the eye. The side channels of different pairs may not overlap with each other, but may be separated from each other.

In accordance with a second variant of the conceivable embodiment of the apparatus according to the first aspect, which may be realized independent from or in combination with the first variant of the conceivable embodiment of the apparatus according to the first aspect, the two or more side channels associated with each of the plurality of insertion channels may respectively extend in a circumferential direction around the point on the axis, e.g., the optical axis, of the eye in the form of the perimeter of a circle segment or of a circle sector. For instance, the two or more side channels associated with each of the plurality of insertion channels may respectively extend in a circumferential direction around the center of the surface of the eye in the form of the perimeter of a circle segment or of a circle sector. For example, the circle segment may be at least substantially in the form of the perimeter of a semi-circle, of a third of a circle or of a quadrant or any other suitable geometrical form.

As a first example, four insertion channels may be placed in the four corneal segments, corresponding to the four segments of the projection of the cornea onto a plane. According to a first variant of the first example, a pair of side channels may circumferentially extend in opposite directions from each of the four insertion channels. According to a second variant of the first example, multiple pairs of side channels may circumferentially extend from each of the four insertion channels. Each pair may be arranged at a different position in the radial direction. It is conceivable that two, three, four or more than four pairs of side channels may extend from each of the four insertion channels. Each side channel of the pairs of side channels may be in the form of substantially a quadrant. In the circumferential direction, the side channels of different pairs may be spaced apart from each other. The channels of a pair of channels may be arranged at the same position in the radial direction. Alternatively, the channels of a pair of channels may be arranged at different positions in the radial direction.

As a second example, two insertion channels may be placed in the two corneal segments, corresponding to the two segments of the projection of the cornea onto a plane. According to a first variant of the second example, a pair of side channels may circumferentially extend in opposite directions from each of the two insertion channels. According to a second variant of the second example, multiple pairs of side channels may circumferentially extend from each of the two insertion channels. Each pair may be arranged at a different position in the radial direction. It is conceivable that two, three, four or more than four pairs of side channels may extend from each of the two insertion channels. Each side channel of the pairs of side channels may be in the form of substantially the perimeter of a semi-circle. In the circumferential direction, the side channels of different pairs may be spaced apart from each other.

The computer may be programmed to control the laser radiation to create in the tissue of the eye at least one insertion channel and the two or more side channels such that the at least one insertion channel and the two or more side channels respectively extend at one depth, different depths and/or varying depths in the eye. For example, each of the at least one insertion channels and/or each of the two or more side channels may lie in one plane. The plane may correspond to the cross-section through the cornea perpendicular to the optical axis of the eye.

As described above, different shapes are conceivable for the at least one insertion channel and the two or more side channels. It is also conceivable to abandon the at least one insertion channel. In this case, for entering the eye, the entrance into the eye may be marked or a centre region of a side channel may be used. For example, the at least one insertion channel and/or the two or more side channels may follow a curved line. The curved line may be created by focusing the laser radiation in the stroma of the tissue with focus points along the curved line. As another example, the at least one insertion channel and/or the two or more side channels may follow a straight line. In this way, a channel shape which departs from the curved line can be created. For all the named channel shapes the at least one insertion channel and/or the two or more side channels can be created with a desired diameter and a desired geometrical configuration through the sequencing of the foci of the laser radiation with sufficiently dose separation through the above-mentioned photodisruption.

Certain embodiments also make it possible to adjust the densities of the at least an insertion channel and/or the two or more side channels in the tissue based on the location in the eye. The term density may be understood as the number of insertion channels and/or side channels per unit area or per unit volume. For example, more insertion channels and/or side channels may be placed at preferred locations in the eye than at others. A greater density of channels at a location allows for a higher density of photosensitizer penetration at the location, which typically yields greater biomechanical and biochemical effects at the location.

Additionally, the density of the photosensitizer effective in the tissue can be controlled by varying the depth of the channels in the cornea. Also, the density of the photosensitizer introduced into the eye can be controlled by choosing a larger or smaller cross-section for the channels. If, for example, a homogeneous distribution of the photosensitizer is required, the density of the channels may substantially be homogeneous in the region of the cornea being treated. One embodiment of certain embodiments may be so designed that the at least one insertion channel and/or the two or more side channels essentially traverse the whole radial area of the cornea with substantially uniform channel density. This means, in other words, that in at least one specified area at a specified depth of the cornea, photosensitizer is brought into the corneal tissue homogeneously (uniformly with the same density) by diffusion.

Provision is made for the at least one insertion channel being connected to more than one opening, i.e., two or more openings, these openings may reaching into the surface of the eye. In this way, for example, a cannula device as set forth below may be inserted into the at least one insertion channel, so that photosensitizer can be brought without hindrance into the two or more side channels extending away from insertion channel into which the cannula device is inserted.

According to a second aspect, a cannula device for introducing photosensitizer into tissue of an eye is provided. The cannula device comprises two or more outlet openings for introducing the photosensitizer into the eye. The two or more outlet openings may be arranged at the side surface of the cannula device. It is conceivable that at least a subset, for example, two, of the two or more outlet openings may be arranged opposite to each other.

According to a specific possible embodiment of the cannula device, a first subset of the two or more outlet openings may be arranged at the side surface of the cannula device at a first position along the longitudinal axis of the cannula device and a second subset of the two or more outlet openings may be arranged at the side surface of the cannula device at a second position different from the first position along the longitudinal axis of the cannula device. Additional subsets may be provided at further positions different from the first and second positions. The first subset and/or the second subset may comprise any number of outlet openings, e.g., two, three, four or more than four outlet openings. For example, the first and/or second subsets may be a pair of outlet openings.

According to a third aspect, a system for dissecting an eye for the introduction of a photosensitizer into tissue of the eye is provided. The system comprises the apparatus as described herein and the cannula device as described herein.

The channel system and the cannula device may be adapted to each other. For example, one of a plurality of cannula devices may be chosen that fits the created channel system. It is conceivable that a plurality of different cannula devices may be provided dependent on the number and/or shape of the channels. For example, a suitable cannula device may be used dependent on the exact configuration of the created channel system.

The cross-section of the cannula device may be adjusted to the cross-section of the insertion channel and the position of the two or more outlet openings along the longitudinal axis of the cannula device may be adjusted to the position of the two more side channels in the radial direction. To give an example, the cross-section of the cannula device may correspond to the cross-section of the insertion channel. Alternatively or additionally, the number and/or position of the two or more outlet openings may correspond to the number of side channels extending away from the insertion channel, in which the cannula device is to be inserted.

According to a fourth aspect, a method for dissecting an eye for the introduction of a photosensitizer into tissue of the eye is provided. The method comprises the steps of: (i) providing laser radiation, (ii) guiding and focusing the laser radiation with respect to the tissue of the eye, and (iii) controlling the laser radiation to create in the tissue of the eye at least one insertion channel which extends at least partially in the stroma of the eye, wherein the at least one insertion channel is connected to at least one opening in the surface of the eye and extends substantially in radial direction with respect to a point on an axis of the eye. The method further comprises the step of controlling the laser radiation to create in the tissue of the eye two or more side channels associated with the at least one channel. The two or more side channels respectively extend away from the associated at least one insertion channel in a direction different from the radial direction.

According to a variant of the method according to the fourth aspect, a method is taught combining the aforementioned method of dissecting any eye with a method of introducing a photosensitizer into a cornea of an eye. The variant of the method according to the fourth aspect may be combined with refractive surgery performed at the cornea, for example, refractive surgery in the form of LASIK.

Certain embodiments will now be explained in more detail making reference to the drawings, in which.

Figure 1:
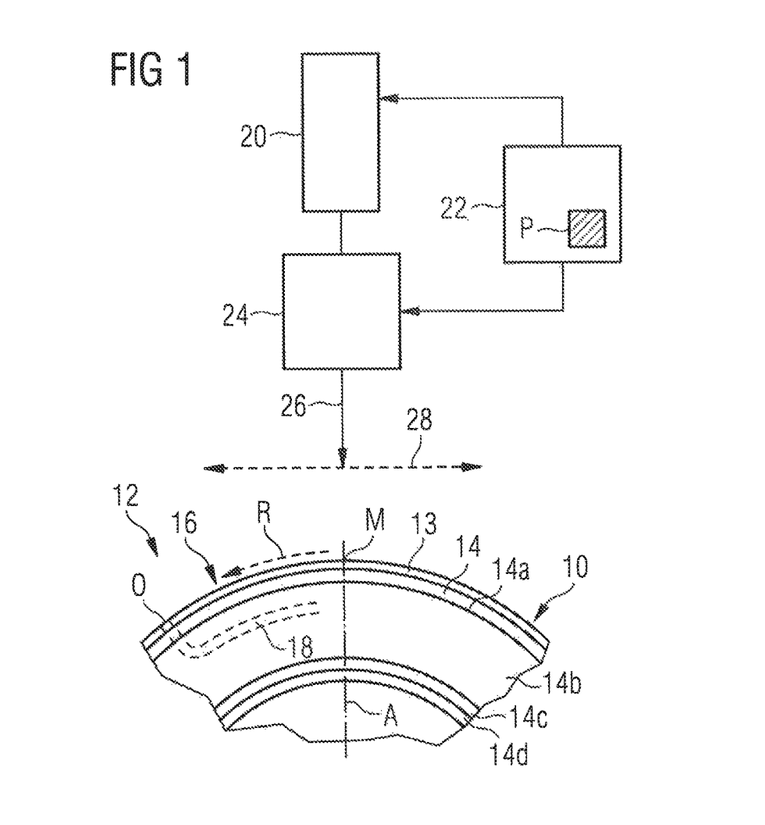
FIG. 1 shows schematically an apparatus for dissecting an eye for the introduction of a photosensitizer into tissue of the eye.

FIG. 1 shows schematically an eye 10. A photosensitizer can be introduced into the eye 10 to change the biomechanical and/or biochemical properties of the eye 10 in a process known as "corneal crosslinking". For example, the mechanical stability of the cornea can be strengthened by the crosslinking.

An eye axis, which in the example shown corresponds to the optical axis of the eye, is labeled "A". The eye axis very nearly coincides with the optical axis of the system for guiding and focusing laser radiation described in more detail below.

The centre (midpoint) of the surface of the cornea (16) is labeled "M". A radial direction R can be defined starting from the centre. The eye to be treated by crosslinking in this example, without limitation, is essentially the cornea 16, which is covered externally by a tear film 13. The cornea 16 has an epithelium 14, a Bowman layer 14a, a stroma 14b, a Decement membrane 14c and an endothelium 14d.

Insertion channels 18 can be introduced into the stroma 14b of the cornea 16 with the apparatus described in more detail below. These insertion channels 18 are in contact with openings O. The openings O provide access from the outside into the channels for inserting a cannula device to be described in more detail below.

In addition the insertion channels 18, side channels 19 (cf. FIG. 2) can be introduced into the stroma 14b of the cornea 16 with the apparatus described in more detail below. These insertion channels 19 are respectively in fluid-conducting contact with one of the insertion channels 18 to which they are associated. The side channels 19 extend away from the associated insertion channel 18.

A photosensitizer can be introduced into the channels 19. The photosensitizer then penetrates into and through the channels and from there distributes itself in the corneal tissue by diffusion. The device has a source 20 for laser radiation, e.g., a femtosecond laser, described above, such as is used, e.g., for cutting a flap/cap in LASIK. An example of the optical system 24 for guiding and focusing the laser radiation 26 inside the cornea 16 is the system used to perform similar operations in LASIK.

In comparison to LASIK, a computer 22 controls the laser radiation source 20 and the optical system 24 for guiding and focusing the laser radiation 26. The computer 22 is programmed with a program P which controls the laser radiation 26 in a special way to create the incision in the cornea 16. In contrast to the LASIK, the incisions are insertion channels 18 and side channels 19. For this the laser radiation 26 undergoes a parallel displacement in the direction of the arrow 28 when creating the aforesaid channels 18 according to FIG. 1. The representation in FIG. 1 shows a view of the eye cut by a plane which contains the axis A. FIG. 1 also shows an insertion channel 18 which extends e.g., substantially parallel to the surface of the cornea 16. The channel is accessible from the outside via an opening O located e.g., near the limbus. A fine syringe or cannula can, for example, be introduced into the opening O so as to be inserted into the insertion channel 18.

Figure 2:
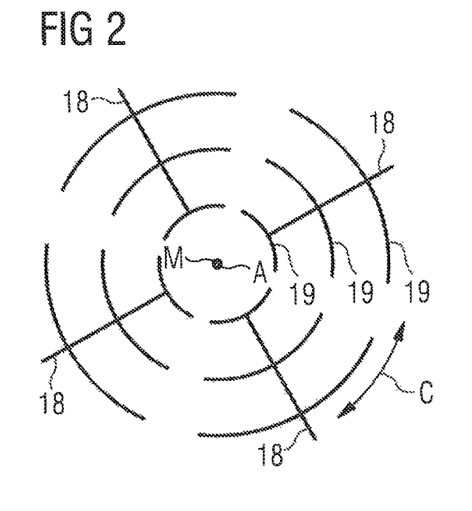
FIG. 2 shows a plan view of a cornea with a schematic description of the creation of channels therein.

FIG. 2 shows a plan view of a cornea 16. As shown in FIG. 2, four insertion channels 18 extend inside the cornea 16 in the radial direction with respect to a projection of the center M into the plane or a point on the eye axis A. The branching points, at which the side channels 19 respectively extend away from the insertion channels 18, of neighboring insertion channels 18 may be arranged at an angle of 90 degrees from each other. All of the four insertion channels 18 may be accessible from the outside by means of four openings (which may be similar to the opening O shown in FIG. 1) which are distributed at equal intervals in the peripheral or circumferential direction C. The radially arranged insertion channels 18 may be arranged in a horizontal plane. For example, the horizontal plane may be perpendicular to the eye axis A. As a variant, the insertion channels 18 may be arranged at varying depths. The choice of location and the path followed by the insertion channels 18 can depend on the respective medical indication and can be chosen accordingly.

In the exemplary configuration shown in FIG. 2, three pairs of side channels 19 respectively extend away from each of the four insertion channels 18. However, any number of pairs of side channels 19 may extend away from each of the insertion channels 18. Each of the side channels 19 extends in the circumferential direction C. In the example shown in FIG. 2, the side channels 19 are in the form of the perimeter of a segment of a geometrical form. More particularly, the side channels 19 exemplarily shown in FIG. 2 are substantially in the form of the perimeter of a quarter-circle. Although by way of example quarter-circles are shown in FIG. 2 to illustrate a possible arrangement of the side channels 19, the side channels 19 may have any other circular or non-circular form. The side channels 19 or a pair of side channels 19 extend in substantially the opposite direction. The three pairs of side channels 19 associated with each insertion channel 18 are positioned at different positions in the radial direction, i.e., at different positions along the insertion channel 18 which they are associated.

In the exemplary configuration shown in FIG. 2, the insertion channels 18 are so configured and positioned that a cannula device can be inserted into each of the insertion channels 18. Outlet openings of the cannula device(s), which are described in more detail below, inserted into the insertion channel(s) 18 can then be brought into fluid-conducting contact with a subset or all of the side channels 19. In this way, the photosensitizer can be introduced from the cannula device(s), through the outlet openings, into the side channels 19. The side channels 19 are so configured and positioned that the photosensitizer distributes itself homogeneously by diffusion in the corneal tissue.

The side channels 19 have a contour which is shaped somewhat like the sector of a circle (as shown). As is shown in FIG. 2, three pairs of side channels 19, which are formed as the perimeter of a sector, can be formed from each insertion channel 18. Each of these pairs of side channels 19 have the same sector angle which is less than 90 degrees.

Figure 3:
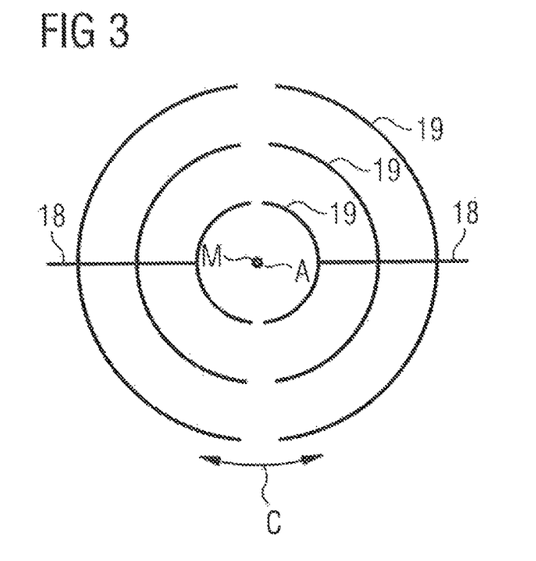
FIG. 3 shows a plan view of a cornea with another schematic description of the creation of channels therein.

An exemplary modification of the channel system of FIG. 2 is shown in FIG. 3, in which only two insertion channels 18 are positioned in the radial direction with respect to a projection of the center M into the plane or a point on the eye axis A. Again, three pairs of side channels 19 extend away from each of the two insertion channels 18, without overlapping or coming in contact with each other.

The branching points, at which the side channels 19 respectively extend away from the insertion channels 18, of the neighboring insertion channels 19 are arranged at an angle of 180 degrees from each other. All of the two insertion channels 18 are accessible from the outside by means of two openings (similar to the openings O of FIG. 1) which are distributed at equal intervals in the peripheral direction C.

Exemplarily and without limitation, three pairs of side channels 19 respectively extend away from each of the two insertion channels 18. Each of the side channels 19 extends in the circumferential direction C. In the specific example shown in FIG. 3, the side channels 19 are in the form of the perimeter of a segment of a circle. More particularly, the side channels 19 exemplarily shown in FIG. 3 are substantially in the form of the perimeter of a semi-circle. The side channels 19 of a pair of side channels extend in substantially the opposite direction. The three pairs of side channels 19 associated with each insertion channel 18 are positioned at different positions in the radial direction, i.e. at different positions along the insertion channel 18 with which they are associated.

The side channels have a contour which is shaped somewhat like the perimeter of the sector of a circle (as shown) for treating astigmatism or higher order aberrations. As is shown in FIG. 3, three pairs of the side channels 19, which are formed as the perimeter of the sector, can be formed from each insertion channel 18. Each of these pairs of side channels 18 have the same sector angle which is less than 180 degrees.

Through the choice of the diameters and the geometric arrangement of the channels, the distribution of photosensitizer in the cornea can be controlled as desired, depending on the medical indication.

The channels are formed by focused laser radiation, in particular by means of a femtosecond laser, through LIOBs created by the laser foci. In certain cases, adjacent cavitation bubbles do not overlap completely, so that some tissue remains between the individual cavitation bubbles. This tissue stabilizes the overall tissue in the structure while being sufficiently permeable as regards the diffusion of photosensitizer in the channels.

Instead of long channels it is also possible to create cavities with other shapes, in particular planar cavities in which e.g., tissue regions spaced uniformly and dose together remain as "posts" between the upper and lower surfaces of the cavity or cavities.

Figure 4:
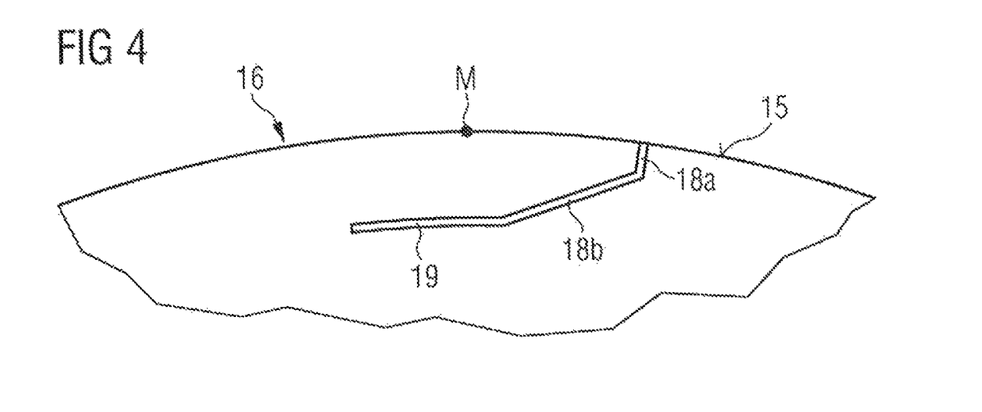
FIG. 4 shows an axial sectional view of a cornea with a channel whose path is at different depths relative to the surface of the cornea.

FIG. 4 schematically shows possible cutting planes of the insertion channel 18 and the side channels 19 which extend at different depths in relation to the surface 15 of the cornea 16. Three different depths for the insertion channel 18 and the side channels 19 are exemplarily shown schematically in FIG. 4. The different depths can be realized for all the structures and arrangements of channels described individually according to FIGS. 1, 2, 3 described above and FIGS. 5*a*-*d* described below as well as other embodiments.

An insertion portion 18*a* may be cut for introduction of the insertion channel 18 or the channel may start also directly with a sloped part 18*b* of the insertion channel 18 on the surface 15 of the cornea 16. The insertion portion 18*a* provides a step to the surface 15 of the cornea 16. In the shown example of FIG. 4, the insertion portion 18*a* is substantially perpendicular to the surface 15 of the cornea 16. Further, the sloped part 18*b* of the insertion channel 18 is shown, which is sloped with respect to the insertion portion 18*a* and with respect to a horizontal plane through the center M. Further, a side channel 19 is shown, which is essentially parallel to said horizontal plane. The sloped part 18*b* extends in a sloped manner from the insertion portion 18*a* to the side channel 19, which lies deeper in the cornea 16. A cannula device can easily be inserted through the insertion portion 18*a* into the sloped part 18*b* of the insertion channel 18.

Figure 5A:
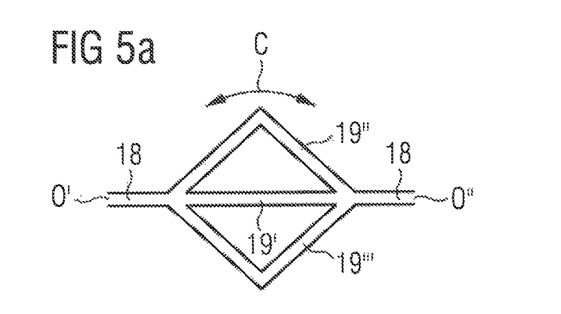
FIG. 5a shows a plan view of a cornea with another schematic description of the creation of channels therein.

Further exemplary modifications of a channel system are shown in FIGS. 5*a* to 5*d*. In FIG. 5*a*, an insertion channel is provided at a first opening O' and a second opening O". The insertion channel 18 extends radially from the first opening O' in the direction of the second opening O". Three side channels 19', 19", 19''' extend away from the insertion channel close to the first opening O'. Two of said three side channels 19', 19", 19''', i.e., outer side channels 19", 19''', are arranged substantially in an angular form. Said two side channels 19", 19''' together substantially have the form of a rhombus. A third of said three side channels 19', 19", 19''', i.e., a middle side channel', extends from the insertion channel 18 that is connected to the first opening O' to the insertion channel 18 that is connected to the second opening O". Said middle side channel 19' lies between said outer two side channels 19", 19'''.

Figure 5B:
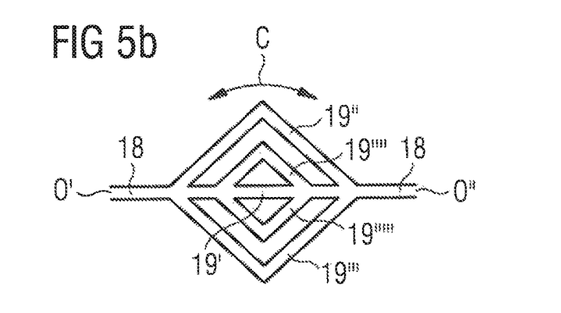
FIG. 5b shows a plan view of a cornea with another schematic description of the creation of channels therein.

The channel system shown in FIG. 5*b* is based on that of FIG. 5*a*. In addition to the channel system shown in FIG. 5*a*, two further side channels 19'''', 19''''' are provided. The two further side channels 19'''', 19''''' are arranged substantially in an angular form, respectively. The two further side channels 19'''', 19''''' are respectively connected at both ends to the middle side channel 19', i.e., the further side channels 19'''', 19''''' respectively extend away from the middle side channel 19' and reenter the same middle side channel 19'.

Figure 5C:
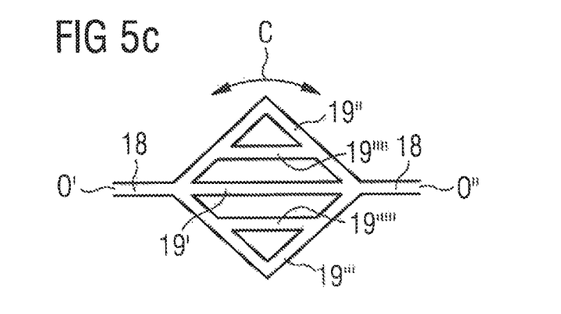
FIG. 5c shows a plan view of a cornea with another schematic description of the creation of channels therein.

The channel system shown in FIG. 5*c* is based on that of FIG. 5*a*. In addition to the channel system shown in FIG. 5*a*, two further side channels 19'''', 19''''' are provided. The two further side channels 19'''', 19''''' are arranged substantially in parallel to the middle side channel 19', respectively. The two further side channels 19'''', 19''''' are respectively connected at both ends to one of the outer side channels 19", 19'''. In other words, one of the further side channels 19'''' extends away from one of the outer side channels 19" and reconnects to the one of the outer side channels 19", and the other of the further side channels 19''''' extends away from the other of the outer side channels 19''' and reconnects to the other of the outer side channels 19'''.

Figure 5D:
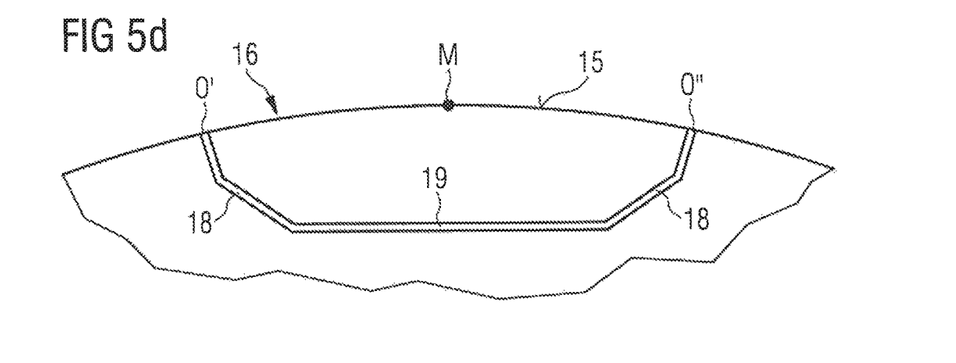
FIG. 5d shows an axial sectional view of a cornea with a channel whose path is at different depths relative to the surface of the cornea.

FIG. 5*d* schematically shows possible cutting planes of the insertion channel 18 and the side channels 19 of the channel system of FIG. 5*a* which extend at different depths in relation to the surface 15 of the cornea 16. As described with respect to FIG. 4 above, an insertion portion may be cut for introduction of the insertion channel 18 or the channel may start also directly with a sloped part of the insertion channel 18 on the surface 15 at both openings O', O". The insertion portion provides a step to the surface 15 of the cornea 16. In the shown example of FIG. 5*d*, the insertion portion is substantially perpendicular to the surface 15 of the cornea 16. Further, the sloped part of the insertion channel 18 is sloped with respect to the insertion portion and with respect to a horizontal plane through the center M. Further, the side channel 19 is shown, which is essentially parallel to said horizontal plane. A cannula device can easily be inserted through the opening O and further through the insertion portion and the sloped part of the insertion channel 18.

As described with respect to FIGS. 2 and 3, a cannula device can be inserted into the insertion channel 18 shown in FIGS. 5*a* to 5*d* and the photosensitizer can be introduced into the side channels 19. The photosensitizer can distribute through the side channels 19 and can then exit the cornea 16 through the opening O". In this way, the pressure in the inside of the channels and the channel system is reduced. In consequence, the risk of damaging tissue because of high pressure in the tissue of the eye is minimized or at least reduced.

Figure 6A:
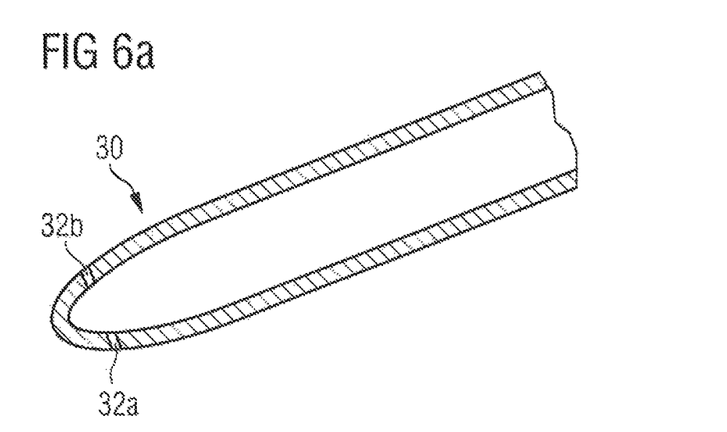
FIG. 6a shows schematically a cannula device for introducing a photosensitizer into tissue of the eye.
Figure 6B:
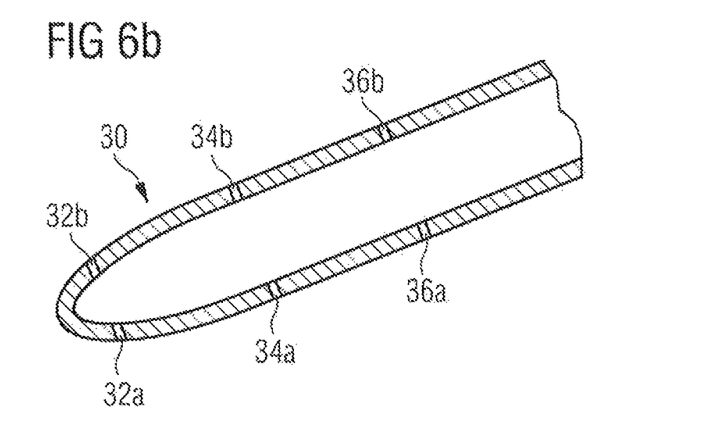
FIG. 6b shows schematically a modification of the cannula device of FIG. 6a for introducing a photosensitizer into tissue of the eye.

FIGS. 6*a* and 6*b* both show exemplary configurations for a cannula device 30 for providing a photosensitizer.

The cannula device 30 shown in FIG. 6*a* exemplarily comprises two outlet openings 32*a*, 32*b* which are arranged at the side surface of the cannula device 30. In the example shown in FIG. 6*a*, the outlet openings 32*a*, 32*b* are arranged opposite to each other. In other words, the outlet openings 32*a*, 32*b* may be arranged at the same position in the longitudinal direction of the cannula device 30. Alternatively, the outlet openings 32*a*, 32*b* may be arranged at different positions in the longitudinal direction of the cannula device 30. For example, the cannula device 30 may be adapted to the arrangement of the side channels 19 as shown in FIGS. 2, 3, 5a, 5b and 5c, e.g., the position of the outlet openings 32a, 32b in the longitudinal direction of the cannula device 30 may correspond to the position of the side channels 19. It is conceivable that a plurality of cannula devices is provided which are suitable for different channel patterns. It is alternatively conceivable that a cannula device, e.g., the position of the outlet openings in the cannula device, can be selectively adjusted dependent on the channel patterns.

The cannula device 30 shown in FIG. 6a is adapted for being inserted into the insertion channel 18 of each of the channel systems shown in FIGS. 2, 3, 5a, 5b and 5c. For example, the cross-section and/or diameter of the cannula device 30 may be configured to be inserted into the insertion channel 18 of said channel systems without damaging the eye.

The cannula device 30 can be inserted into one of the insertion channels 18 shown in FIG. 2 such that each of the two outlet opening 32a, 32b come into fluid conducting contact with each of the side channels 19 of one of the three pairs of side channels 19. It is possible for the cannula device 30 to have a round top at its tip or end portion. The tip or end portion may also be referred to as insertion portion. For example, the cannula device 30 can be inserted into the upper right of the four insertion channels 18 in the radial direction until the outlet openings 32a, 32b come into fluid-conducting contact with the outer side channels 19 extending away from the upper right insertion channel 18. The photosensitizer can then be introduced into said outer side channels 19 associated with the upper right insertion channel 18 through the outlet openings 32a, 32b. Afterwards, the cannula device 30 can be introduced further into the radial direction through the upper right insertion channel 18 until the outlet openings 32a, 32b come into fluid-conducting contact with the side channels 19 of the middle pair of side channels 19 extending away from the upper right insertion channel 18. Again, photosensitizer can be introduced into said side channels 19, and the cannula device 30 can be moved further into the radial direction and so on.

Instead of having a round top, the cannula device 30 may alternatively be configured to have a sharp top at its tip or end portion. This configuration may allow insertion of the cannula device even in the absence of any insertion channel 18.

FIG. 6b shows a cannula device 30 according to an exemplary modification of the cannula device 30 of FIG. 6a. The modified cannula device 30 of FIG. 6b comprises multiple pairs of outlet openings. In the exemplary configuration shown in FIG. 6b, the cannula device 30 comprises three pairs of outlet openings and thus six outlet openings 32a to 36b. However, the number of three pairs of outlet openings is given here merely as an example but without limitation. For example, the distance between the pairs of outlet openings 32a to 36b along the longitudinal axis of the cannula device 30 may be adapted to the distance between the pairs of side channels 19 shown in FIGS. 2 and 3 associated with one of the insertion channels 18. In the exemplary configuration shown in FIG. 6b, the distance between the most distal pair of outlet openings 32a, 32b and the middle pair of outlet openings 34a, 34b is equal to the distance between the inner pair of side channels 19 and the middle pair of side channels 19 associated with one, e.g., the upper right, of the insertion channels 18 shown in FIGS. 2 and 3. Further, the distance between the middle pair of outlet openings 34a, 34b and the most proximal pair of outlet openings 36a, 36b is equal to the distance between the middle pair of side channels 19 and the outer pair of side channels 19 associated with one, e.g., the upper right, of the insertion channels 18 shown in FIGS. 2 and 3.

The cannula device 30 can be inserted into one of the insertion channels 18 shown in FIGS. 2 and 3 such that the outlet openings 32a to 36b of each pair of outlet openings simultaneously come into fluid-conducting contact with the corresponding side channels 19 of each pair of side channels 19. In other words, all side channels 19 may simultaneously be provided with photosensitizer through the multiple outlet openings 32a to 36b.

A set of different cannula devices 30 may be provided and one or more of the set of cannula devices 30 may be used for insertion into the insertion channels 18 depending on the configuration of the generated channel system.

Certain embodiments also include a method for dissecting an eye for the introduction of photosensitizer where, by means of laser radiation 26 which is focused on and into the cornea. Insertion channels 18 are created in the cornea, wherein the insertion channels 18 extend from the surface 14a of the cornea into the interior of the cornea. Side channels 19 are created which extend away from the insertion channels 18. In this method all the characteristics and properties of the insertion channels 18 and side channels 19 which have been described above can be employed.

10 Eye
13 Tear film
14 Epithelium
14a Bowman's layer
14b Stroma
14c Decement's membrane
14d Endothelium
15 Surface of cornea
16 Cornea
18 Insertion channel
18a Insertion portion of insertion channel
18b Sloped part of insertion channel
19 Side channel
20 Source of laser radiation
22 Computer
24 Optical system
26 Laser radiation
28 Arrow
30 Cannula device
32a-36b Outlet openings
A Axis
C Circumferential direction
M Midpoint or center of the eye
O Openings
O' First opening
O" Second opening
P Program

The invention claimed is:
1. An apparatus for dissecting an eye for the introduction of a photosensitizer into tissue of the eye, the apparatus comprising:
a source of laser radiation;
a system that guides and focuses a laser radiation with respect to the tissue of the eye; and
a computer for controlling said system, the computer being programmed to:
control the laser radiation to create in the tissue of the eye an insertion channel that extends at least partially into the stroma of the eye, the insertion channel connected to at least one opening in the surface of the eye and extending substantially in a radial direction with respect to a point on an axis of the eye; and control the laser radiation to create in the tissue of the eye two or more side channels associated with the insertion channel, the two or more side channels respectively extending away from the insertion channel in a direction different from the radial direction;

wherein a rectilinearly sloped part of the insertion channel extends in a sloped manner with respect to each of a horizontal plane through the center of the cornea and the side channels; and wherein the two or more side channels lie at different depths in the cornea along the rectilinearly sloped part.

2. The apparatus according to claim 1, wherein the two or more side channels respectively extend substantially in a circumferential direction around the point on an axis of the eye.

3. The apparatus according to claim 2, wherein the two or more side channels are circularly shaped.

4. The apparatus according to claim 1, wherein: a first subset of the two or more side channels extend away from the insertion channel in the direction different from the radial direction at a first position along the radial direction; and a second subset of the two or more side channels extend away from the insertion channel in the direction different from the radial direction at a second position along the radial direction different from the first position.

5. The apparatus according to claim 1, wherein the two or more side channels are respectively arranged in a substantially angular shape.

6. The apparatus according to claim 1, wherein a cross-section of the insertion channel is different from a cross-section of the two or more side channels.

7. The apparatus according to claim 6, wherein the cross-section of the insertion channel is larger than the cross-section of the two or more side channels.

8. The apparatus according to claim 1, wherein the computer is programmed to:

control the laser radiation to create in the tissue of the eye a plurality of insertion channels, wherein each of the plurality of insertion channels extends substantially in a radial direction with respect to the point on the axis of the eye, and control the laser radiation to create in the tissue of the eye two or more side channels associated with each of the plurality of insertion channels, wherein the two or more side channels respectively extend away from the associated insertion channel of the plurality of channels in a direction different from the radial direction.

9. The apparatus according to claim 8, wherein the two or more side channels, which are associated with different insertion channels of the plurality of insertion channels, are separated from each other.

10. The apparatus according to claim 8, wherein the two or more side channels of each of the plurality of insertion channels respectively extend in a circumferential direction around the point on the optical axis of the eye in the form of a perimeter of a circles segment.

11. The apparatus according to claim 10, wherein the perimeter of the circle segment is substantially a perimeter of a geometrical form.

12. The apparatus according to claim 8, wherein the computer is programmed to control the laser radiation to create in the eye each of the plurality of insertion channels at a respective segment of a plurality of segments of the eye.

13. The apparatus according to claim 1, wherein the insertion channel and the two or more side channels are at least partially created by laser induced optical breakthrough created by the laser radiation and at least in part do not merge completely with one another, a distance between adjacent laser induced optical breakthrough being in the range from 1 to 20 pm.

14. The apparatus according to claim 1, wherein the source for laser radiation is a femtosecond laser, a nanosecond laser, a picosecond laser, or an attosecond laser.

* * * * *